United States Patent [19]
Verduijn

[11] Patent Number: 5,855,863
[45] Date of Patent: *Jan. 5, 1999

[54] ZEOLITE L PREPARATION

[75] Inventor: Johannes Petrus Verduijn, Spijkenisse, Netherlands

[73] Assignee: Exxon Chemical Patents Inc., Houston, Tex.

[ * ] Notice: The term of this patent shall not extend beyond the expiration date of Pat. No. 5,486,348.

[21] Appl. No.: 461,797

[22] Filed: Jun. 5, 1995

Related U.S. Application Data

[62] Division of Ser. No. 168,970, Dec. 16, 1993, which is a continuation of Ser. No. 600,281, Oct. 17, 1990, abandoned, which is a continuation of Ser. No. 517,959, Apr. 30, 1990, abandoned, which is a continuation of Ser. No. 297,456, Jan. 13, 1989, abandoned.

[30] Foreign Application Priority Data

Jan. 19, 1988 [GB] United Kingdom .................. 8801067

[51] Int. Cl.$^6$ .................................................. C01B 39/32
[52] U.S. Cl. .................................. 423/700; 423/DIG. 28; 502/70; 502/77
[58] Field of Search ........................ 423/700, DIG. 28; 502/70, 77

[56] References Cited

U.S. PATENT DOCUMENTS

| | | |
|---|---|---|
| 3,216,789 | 11/1965 | Breck et al. . |
| 3,650,687 | 3/1972 | McDaniel et al. . |
| 3,867,512 | 2/1975 | Young et al. . |
| 4,104,320 | 8/1978 | Bernard et al. . |
| 4,165,276 | 8/1979 | Antos . |
| 4,206,040 | 6/1980 | Antos . |
| 4,231,897 | 11/1980 | Antos . |
| 4,295,959 | 10/1981 | Antos . |
| 4,295,960 | 10/1981 | Antos . |
| 4,443,326 | 4/1984 | Field . |
| 4,448,891 | 5/1984 | Conon . |
| 4,456,527 | 6/1984 | Buss et al. . |
| 4,458,025 | 7/1984 | Lee et al. . |
| 4,517,306 | 5/1985 | Buss et al. . |
| 4,539,304 | 9/1985 | Field . |
| 4,539,305 | 9/1985 | Wilson et al. . |
| 4,544,539 | 10/1985 | Wortel . |
| 4,547,472 | 10/1985 | Vannordstr . |
| 4,579,831 | 4/1986 | Field . |
| 4,595,670 | 6/1986 | Tauster et al. . |
| 4,608,356 | 8/1986 | Buss et al. . |
| 4,614,834 | 9/1986 | Lambert et al. . |
| 4,648,960 | 3/1987 | Poeppelmeir et al. . |
| 5,486,348 | 1/1996 | Verduijn et al. .................. 423/700 |

FOREIGN PATENT DOCUMENTS

| | | |
|---|---|---|
| 888365 | 7/1981 | Belgium . |
| 40119 | 11/1981 | European Pat. Off. . |
| 96479 | 12/1983 | European Pat. Off. . |
| 107389 | 5/1984 | European Pat. Off. . |
| 109199 | 5/1984 | European Pat. Off. . |
| 142347 | 5/1985 | European Pat. Off. . |
| 142349 | 5/1985 | European Pat. Off. . |
| 142351 | 5/1985 | European Pat. Off. . |
| 142353 | 5/1985 | European Pat. Off. . |
| 142354 | 5/1985 | European Pat. Off. . |
| 142355 | 5/1985 | European Pat. Off. . |
| 145289 | 6/1985 | European Pat. Off. . |
| 16775 | 1/1986 | European Pat. Off. . |
| 184450 | 6/1986 | European Pat. Off. . |

(List continued on next page.)

*Primary Examiner*—Elizabeth D. Wood
*Attorney, Agent, or Firm*—Edward F. Sherer

[57] ABSTRACT

Binderless particles of zeolite L of very high mechanical strength are prepared by a process which comprises forming a mixture by reacting substantially binderless particles of zeolite L, preferably as shaped particles such as extrudates, with an aqueous alkaline solution containing sources of alkali metal, at least 50 mole % of which is potassium, and aluminium to obtain the desired particles of very high mechanical strength. The zeolite L thus obtained can form part of a dehydrocyclisation and/or isomerisation catalyst.

18 Claims, 1 Drawing Sheet

FOREIGN PATENT DOCUMENTS

| | | |
|---|---|---|
| 184451 | 6/1986 | European Pat. Off. . |
| 185519 | 6/1986 | European Pat. Off. . |
| 201856 | 11/1986 | European Pat. Off. . |
| 284206 | 9/1988 | European Pat. Off. . |
| 548567 | 4/1977 | U.S.S.R. . |
| 1316311 | 5/1973 | United Kingdom . |
| 2004764 | 4/1979 | United Kingdom . |
| 1600927 | 10/1981 | United Kingdom . |
| 2106483 | 4/1983 | United Kingdom . |
| 2109359 | 6/1983 | United Kingdom . |
| 2114150 | 8/1983 | United Kingdom . |
| 2116450 | 9/1983 | United Kingdom . |
| 2121427 | 12/1983 | United Kingdom . |
| 2160517 | 12/1984 | United Kingdom . |
| 2142648 | 1/1985 | United Kingdom . |
| 2153384 | 8/1985 | United Kingdom . |
| 2153840 | 8/1985 | United Kingdom . |
| 2166972 | 5/1986 | United Kingdom . |
| 8704365 | 7/1987 | WIPO . |

ZEOLITE L PREPARATION

This application is a Divisional of application Ser. No. 08/168,970, filed Dec. 16, 1993, which is a continuation of Ser. No. 07/600,281, filed Oct. 17, 1990, now abandoned, which is a continuation of Ser. No. 07/517,959, filed Apr. 30, 1990, now abandoned, which is a continuation of Ser. No. 07/297,456, filed Jan. 13, 1989, also abandoned.

BACKGROUND OF THE INVENTION

This invention relates to the preparation of substantially binderless particles of zeolite L, particularly in the form of aggregates for use in catalysis, particularly for aromatisation.

Zeolite L has been known for some time as an adsorbant, and in U.S. Pat. No. 3,216,789 is described as an aluminosilicate of the formula:

$$0.9-1.3\ M_{2/n}O:Al_2O_3:5.2-6.9.SiO_2:yH_2O$$

(where M is an exchangeable cation of valency n and y is from 0 to 9) having a characteristic X-ray diffraction pattern. The preparation of zeolite L is described in U.S. Pat. No. 3,216,789, EP-A-167755, EP-A-142355, EP-A-142347, EP-A-142349, EP-A-109199, PL-A-72149, U.S. Pat. No. 3,867,512, and SU-548567.

EP-A-96479 describes and claims zeolite L having a characteristic morphology and size, which is particularly valuable for use as a catalyst base in hydrocarbon conversions such as aromatisation, and comprising crystallites in the form of cylinders with a mean diameter of at least 0.1 micron, preferably at least 0.5 micron.

EP-A-96479 describes a synthesis of zeolite L which is conducted so that the amount of the contaminant zeolite W, which is know to grow in such a system as a competitive phase, is minimised. A preferred synthesis gel described in EP-A-96479 has the following mole ratios:

$$2.62K_2O:Al_2O_3:10SiO_2:160H_2O$$

and it is discussed how this gel may be varied by changing the molar amount of one component within the following ranges:

| | |
|---|---|
| $K_2O$: | 2.4–3.0 moles |
| $Al_2O_3$: | 0.6–1.3 moles |
| $SiO_2$: | 8–12 moles |
| $H_2O$: | 120–240 moles |

EP-A-142353, EP-A-142354 and EP-A-185519 describe developments of this process for forming cylindrical zeolite L.

Zeolite L may be used as a catalyst base in aromatisation reactions. U.S. Pat. No. 4,104,320 discloses dehydrocyclisation of aliphatic compounds in the presence of hydrogen using a catalyst comprising zeolite L and a group VIII metal. The particular zeolite disclosed in EP-A-96479 is remarkably effective in such aromatisation reactions being capable of forming catalysts which have extended lifetime. Such dehydro- cyclisation and/or aromatisation reactions and catalysts for use in such reactions are also described in EP-A-107389, EP-A-184451, EP-A-142351, EP-A-145289, EP-A-184450, U.S. Pat. No. 4,614,834, GB-A-2116450, GB-A-2114150, U.S. Pat. No. 4,458,025, U.S. Pat. No. 4,456,527, GB-A-2142648, GB-A-2106483, U.S. Pat. No. 4,443,326, GB-A-2121427, GB-A-2153840, GB-A-2153384, U.S. Pat. No. 4,517,306, U.S. Pat. No. 4,539,304, U.S. Pat. No. 4,539,305, U.S. Pat. No. 4,547,472, GB-A-2166972, U.S. Pat. No. 4,579,831, U.S. Pat. No. 4,608,356 and EP-A-201856.

The product recovered from the usual methods used to prepare zeolite L is a fine sized crystalline material. Several of the uses as catalysts or molecular sieves require a product in a size range substantially larger than the size of the product recovered from the preparation processes of the prior art. To meet this demand, various binders are used in forming steps to prepare aggregates containing zeolite L as the principal ingredient such as pellets, extrudates, or tablets. These aggregates lose some of their activity per unit weight since the binder has a different and low activity and acts as a diluent of the molecular sieve activity and the conventionally-bound aggregates frequently do not have sufficient crushing strength, particularly when they contain the cylindrical zeolite L crystallites as described in EP-A-96479. In addition particles made using alumina as binder are susceptible to blocking of the zeolite pores, as a result of alumina migration. It is therefore highly desirable to develop a method of preparing binderless aggregates having a particle size suitable for catalyst or sieve systems and possessing good attrition resistance.

The prior art has developed processes of producing binderless sieve aggregates from silica and alumina starting materials such as silica-alumina catalysts and clay. Unfortunately the products produced by these processes, especially where clay is used as a starting material, generally have very poor attrition resistance and thus rapidly break during use into unsuitable powders which must be replaced.

U.S. Pat. No. 3,650,687 describes processes for the preparation of binderless zeolite particles including zeolite L, in which an alumina silicate clay is slurried with an alkali silicate, spray dried to form particles of the desired finished size and then treated with an alkali and aged to convert the particles to zeolite. In an alternative, a hydrated clay is slurried and spray dried to form particles., then calcined and reacted with the other components necessary to form a zeolite. Thus zeolite is only formed after the final particles have been formed. Predictable formation of zeolite having optimum catalytic properties may be difficult under such circumstances.

Also spray drying can be used only to give small particles, typically of 100 to 400 microns, which are only suitable for fluidised beds whereas reactors usually need particle sizes of at least 0.8 mm, preferably at least 1.5 mm and typically 3 mm.

GB-A-1316311 describes binderless zeolite particles which may be of zeolite L, and which are formed by pelleting, crush and repelleting repeatedly to give products of the desired strength. This is a time-consuming procedure which is costly and can damage the zeolite crystals.

GB-A-2109359 describes the preparation of zeolite 3A and 4A binderless particles in various processes in which kaolin clay and sodium hydroxide (in some cases with zeolite) are formed into beads and then reacted with further sodium hydroxide to form zeolite 4A (sodium form) which is exchanged to form zeolite 3A (potassium form). It is clearly stated that direct formation of a potassium zeolite is not possible in this process.

GB-A-2160517 describes the formation of so called preformed zeolite particles, which may be zeolite L particles prepared from a starting material, which may be a synthetic zeolite but must have a silica/alumina ratio lower than the product. The starting material is reacted with a silica material and an alkali to form the product. To form zeolite L either zeolite 3A, kaolin or a silica-alumina starting material is used. The products are necessarily more silica rich than the starting zeolite. This process has practical handling problems in treating particles with a silica containing material.

The prior art systems are either unsuitable for providing binderless particles of zeolite L having high catalytic or absorbent activity, or result in particles of inadequate strength to be suitable for handling in practical applications or are impractical for large scale operation.

EP-A-284206 (counterpart to U.S. Pat. No. 5,486,348) describes the preparation of binderless zeolite L particles involving the reaction of an alkaline solution comprising a source of alumina with particles formed from silica and 0 to 95 wt % of preformed zeolite L crystallites to convert the silica binder to zeolite L and obtaining the desired particles by crystallisation of the reaction mixture.

The present invention concerns a method of preparing binderless zeolite L particles with further enhanced catalytic performance and/or capacity over those prepared by the process of EP-A-284206 and with very high mechanical strength, for example against attrition. The invention also provides certain novel binderless zeolite L particles.

SUMMARY OF THE INVENTION

According to this invention binderless particles of zeolite L of very high mechanical strength are prepared by a process comprising reacting substantially binderless particles of zeolite L with an aqueous alkaline solution containing sources of alkali metal and aluminium to obtain the desired particles of very high mechanical strength, wherein at least 50 mole % of the alkali metal is potassium.

BRIEF DESCRIPTION OF THE DRAWING

The FIGURE shows scanning electron micrographs of the interior of the starting and product extrudates prepared in Example 1.

DETAILED DESCRIPTION OF THE INVENTION

Figure 1:
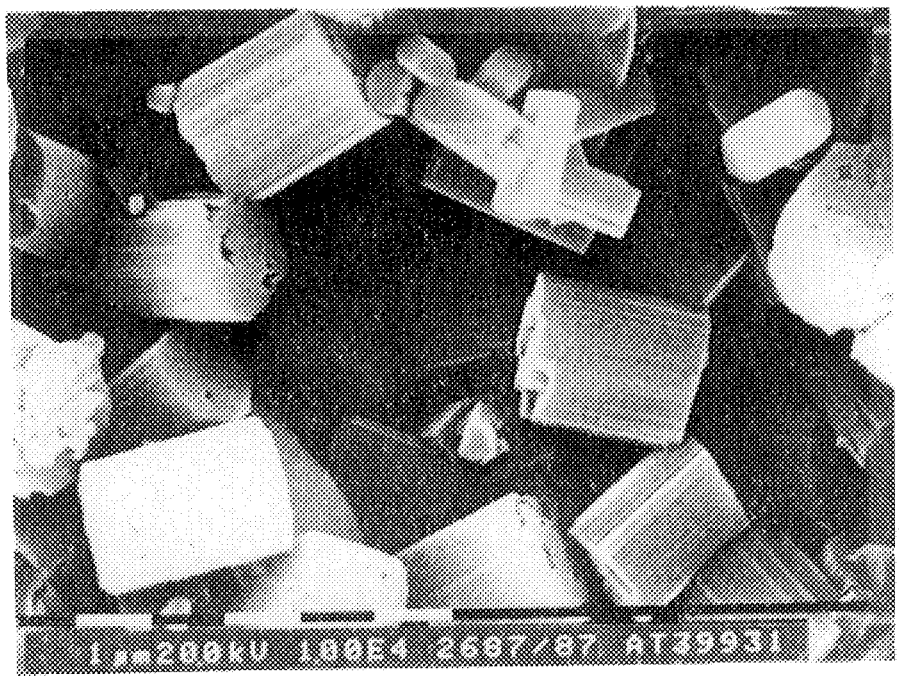
Figure 2:
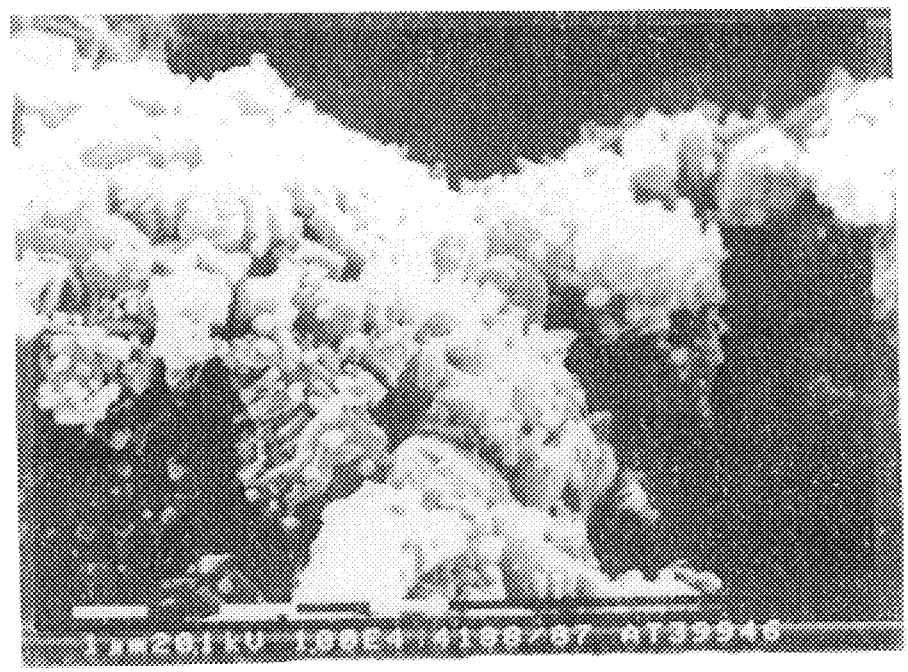

When used herein in relation to the invention the terms "binderless zeolite L particles" or "binder-free zeolite L particles" refer to a plurality of individual zeolite L crystallites held together without the use of a significant amount of non-zeolitic binder. Preferably the particles contain less than 10 wt % (based on the weight of the total particles) of non-zeolitic binder. More preferably, the particles contain less than 5 wt % of non-zeolitic binders, and it is most preferable for the particles to be substantially free of non-zeolitic binder. Although any particles, e.g. powders or crushed shaped particles, may be used as starting material, preferably they are shaped particles, e.g. as tablets or pellets and they are usually formed by extrusion.

The binderless particles or binderless shaped particles of zeolite L used as the starting material for the process of this invention are preferably obtained by the process of EP-A-284206. In that process the zeolite L crystallites are used as starting material which in turn may be prepared by any of the known procedures. However preferably in that process the zeolite L comprises crystallites in the form of cylinders with a mean diameter of at least 0.05 micron, preferably at least 0.1 micron, typically at least 0.5 micron (such as described in EP-A-96479), and most preferably the crystallites have the basal planes shaped such that the ratio of axial length of curved cylindrical surface (1) to the overall axial length of the crystallite (h) is greater than 0.9, optimally substantially unity. Also however one may use XRD—substantially invisible material prepared by the process of patent application Ser. No. 292,704, now U.S. Pat. No. 5,064,630.

The zeolite L used as starting material, and in the final particle of the process of EP-A-284206, is preferably an aluminosilicate and although described as an aluminosilicate, other elemental substitutions are possible; for example aluminium may be substituted by gallium, boron, iron and similar trivalent elements, and silicon may be substituted by elements such as germanium or phosphorus. The aluminosilicates preferably have a composition (expressed in terms of molar ratios of the constituent oxides in anhydrous form) of:

$$(0.9-1.3) \; M_{2/n}O:Al_2O_3:xSiO_2 \quad (I)$$

wherein M is a cation of valence n, x is from 4 to 7.5.

For the purpose of the present invention, the exchangeable cation M comprises potassium, although it is possible for a part of the potassium to be replaced by other cations such as alkali and alkaline earth metals for example sodium, rubidium or caesium. The zeolite L may also contain, preferably at non-exchangeable sites, copper, magnesium, calcium, barium, lead, iron, manganese, chromium, cobalt, nickel or zinc.

Although according to the present invention the starting material, i.e. binderless particles of zeolite, preferably in the form of shaped particles, such as extrudates, are obtained by the process described in EP-A-284206, any binderless zeolite L starting materials may be used.

According to the present invention the binderless particles of zeolite L are mixed with an aqueous alkaline solution containing sources of alkali metal and aluminium. It is preferred that the alkali metal is entirely potassium or potassium together with other metals such as caesium, lithium or rubidium. In the case where other metals are present there must be at least 50 mole % of potassium present. Particularly suitable is a mixture of potassium and caesium ions.

The source of alkali metal in the reaction mixture is preferably obtained by using the alkali metal hydroxide, but one can use other salts such as the chloride, fluoride or nitrate, provided that the solution is alkaline. When mixtures of alkali metal ions are used the molar ratio expressed as oxide $K_2O/(M_2O+K_2O)$, M being alkali metal other than K, is preferably between 0.7 and 1.0.

Preferably, the alkalinity of the reaction mixture, expressed as $K_2O/H_2O$ molar ratio is from 0.007 to 0.028, and more preferably between 0.011 and 0.022.

The source of aluminium is preferably obtained by using alumina or aluminium hydroxide. If the source of alkali metal is obtained by the use of alkali metal oxide, hydroxide or carbonate then aluminates can be formed by using aluminium metal.

It is desirable that the concentration of aluminium in the aqueous solution is such that expressed as $Al_2O_3$ the molar ratio of $Al_2O_3$ to water is at least 0.0015 and preferably between 0.002 and 0.006.

The binderless particles or shaped particles of zeolite L are mixed with the aqueous solution containing alkali metal and aluminium such that the binderless particles are at least wetted by the aqueous solution.

To obtain the desired particles of very high mechanical strength, this mixture is heated in an autoclave to bring about re-crystallisation.

This treatment is generally carried out in a sealed autoclave and thus at autogenous pressure. It is generally inconvenient, although possible to employ higher pressures. Lower pressure (and lower temperature) will require longer re-crystallisation times.

Crystallisation time is related to the crystallisation temperature. The re-crystallisation is preferably carried out at from 100° C. to 200° C. and at this temperature the crystallisation time is typically from 12 hours, e.g. 15 to 96 hours.

Following the preparation as described above the zeolite may be separated, washed and dried in the normal manner.

The product of the invention shows aluminium enrichment compared with the starting material and scanning electron micrographs of the product of this invention show the presence of newly formed submicron crystals. It appears that the aluminium enrichment and/or the presence of these submicron crystals within the extrudates increases the mechanical strength.

If the starting material is crushed particles the final product is also particulate. However this particulate product can be turned into shaped particles by the use of conventional binder techniques or by the binderless process disclosed in EP-A-284206.

The binderless zeolite L particles prepared by the invention are excellent catalyst bases and may be used in conjunction with one or more catalytically-active metals in a wide variety of catalytic reactions. The particular morphology of the crystals appears to result in a particular stable base for catalytically active metals with a surprising resistance to metal catalyst deactivation. The product has shown an increased $SiO_2/Al_2O_3$ ratio which is believed to contribute to the enhanced performance. Also the particles have increased toluene adsorption capacity as compared to conventionally bound zeolite L, together with increased particle strength. In addition, they have displayed low acidity which makes them especially suited to catalytic applications where a low acid site strength is advantageous such as aromatisation.

The catalytically-active metal(s) may be, for example, a Group VIII metal such as platinum, or tin or germanium as described in U.S. Pat. No. 4,104,320, or a combination of platinum and rhenium as described in GB-A-2004764 or BE-A-888365. In the latter case, the catalyst may for appropriate circumstances also incorporate halogen as described in U.S. Pat. No. 4,165,276, silver as described in U.S. Pat. No. 4,295,959 and U.S. Pat. No. 4,206,040, cadmium as described in U.S. Pat. No. 4,295,960 and U.S. Pat. No. 4,231,897 or sulphur as described in GB-A-1600927.

We have found a particularly advantageous catalyst composition to incorporate from 0.1 to 6.0 wt. %, preferably from 0.1 to 1.5 wt. % platinum or palladium, since this gives excellent results in aromatisation. From 0.4 to 1.2 wt. % platinum is particularly preferred, especially in conjunction with the potassium form of the aluminosilicates. The invention extends to catalysts comprising the zeolitic material and a catalytically-active metal.

The products of the invention may be used in a process for the conversion of a hydrocarbon feed in which the feed is contacted with a catalyst as described above under appropriate conditions to bring about the desired conversion. They may, for example, be useful in reactions involving aromatisation and/or dehydrogenation reaction. They are particularly useful in a process for the dehydrocyclisation and/or isomerisation of acyclic hydrocarbons in which the hydrocarbons are contacted at a temperature of from 370° to 600° C., preferably 430° to 550° C., with a catalyst comprising binderless zeolite L particle of the invention, preferably having at least 90% of the exchangeable cations as alkali metal ions, and incorporating at least one Group VIII metal having dehydrogenating activity, so as to convert at least part of the aliphatic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred aspect the feed to a process for preparing aromatic hydrocarbons and particularly benzene comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320, BE-A-888365 or EP-A-40119.

As shown in EP-A-96479, the use of zeolite L with cylindrical morphology enables greatly improved catalyst lifetimes to be achieved as compared to the lifetime obtained with a zeolite L, prepared according to the procedures described in the art prior to EP-A-96479. The invention enables microscopic particles to be prepared from such cylindrical zeolite L, without the use of binder to dilute the performance of the cylindrical crystallites.

The invention is now illustrated by the following Examples.

EXAMPLE 1

Treatment of binderfree zeolite L extrudates with potassium-aluminate solution.

Preparation of the synthesis mixture (weight of reactants are given in grams)

| | |
|---|---|
| KOH pellets (87.3%) | 5.150 |
| Al(OH)$_3$ (98.6%) | 2.231 |
| H$_2$O | 11.51 |
| additional water | 20.71 |

The aluminium hydroxide was dissolved by boiling and after cooling the aluminate solution was poured into a 150 ml stainless steel autoclave together with the additional water. Next, 20.02 grams of binderfree zeolite L extrudates were added to the contents of the autoclave.

The reaction mixture was subjected to treatment for 69.5 hrs at 150° C.

Washing and Drying:

The product-extrudates were washed with 9 portions of water until a pH of 9.5 was obtained. The total washing time was 25 hours. The product-extrudates were dried at 150° C. for 20 hrs. The weight of the recovered extrudates as 22.70 grams.

Characterisation:

TGA—toluene adsorption capacity at 30° C. and at p/po= 0.25:6.5 wt %.

X-Ray diffraction: XRD showed that the product consisted of zeolite L. The apparent XRD-crystallinity versus the starting binderfree extrudates was 82%. This loss in XRD-crystallinity may be due to the presence of the newly formed submicron crystals. It was observed that there was a considerable shift in the d-values compared with those of conventionally prepared zeolite L and this is believed to be due to the aluminium enrichment. Comparative X-Ray data of this product and of conventional zeolite L are given in the Table.

Scanning Electron Micrographs: SEM micrographs showing the interior of the starting extrudates and of the product-extrudates are given in the FIGURE. The micrographs clearly show the presence of the newly formed submicron crystals.

TABLE

| Conventional Zeolite L | | Binderfree Zeolite L of this Invention | |
|---|---|---|---|
| 2 THETA | d(Å) | 2 THETA | d(Å) |
| 5.538 | <u>15.9446</u> | 5.404 | <u>16.3378</u> |
| 11.088 | 7.9725 | 9.449 | 9.3519 |
| 11.730 | 7.5380 | 10.908 | 8.1039 |
| 14.703 | 6.0197 | 11.663 | 7.5811 |
| 15.192 | 5.8268 | 12.598 | 7.0204 |
| 19.301 | <u>4.5948</u> | 14.481 | 6.1113 |
| 20.092 | 4.4156 | 15.055 | 5.8796 |
| 20.460 | 4.3369 | 19.016 | <u>4.6629</u> |
| 22.653 | <u>3.9218</u> | 19.815 | 4.4766 |
| 23.339 | 3.8082 | 20.251 | 4.3812 |
| 24.274 | <u>3.6636</u> | 22.416 | <u>3.9627</u> |
| 25.566 | <u>3.4812</u> | 23.095 | 3.8478 |
| 26.171 | 3.4021 | 24.215 | <u>3.6723</u> |
| 27.121 | <u>3.2850</u> | 25.460 | <u>3.4954</u> |
| 28.003 | <u>3.1836</u> | 26.823 | <u>3.3208</u> |
| 29.081 | <u>3.0679</u> | 27.638 | <u>3.2248</u> |
| 29.680 | 3.0074 | 28.904 | <u>3.0863</u> |
| 30.679 | <u>2.9117</u> | 29.300 | 3.0455 |
| 31.230 | 2.8616 | 30.501 | <u>2.9282</u> |
| 31.514 | 2.8364 | 31.161 | 2.8677 |
| 32.023 | 2.7925 | 31.650 | 2.8245 |
| 33.521 | 2.6710 | 33.130 | 2.7017 |
| 33.756 | 2.6530 | 33.335 | 2.6855 |
| 34.193 | 2.6201 | 33.994 | 2.6387 |
| 35.859 | 2.5020 | 35.451 | 2.5299 |
| 36.317 | 2.4715 | 35.904 | 2.4990 |
| 37.018 | 2.4263 | 36.539 | 2.4570 |
| 37.201 | 2.4148 | 36.786 | 2.4411 |
| 39.191 | 2.2967 | 37.532 | 2.3943 |
| 39.598 | 2.2740 | 38.712 | 2.3240 |
| 41.038 | 2.1975 | 39.145 | 2.2992 |
| 44.383 | 2.0393 | 40.584 | 2.2210 |

The d-values of the most intense peaks are underlined.

EXAMPLE 2

Treatment of binderfree zeolite L extrudates with potassium hydroxide solution.

Example 1 was repeated using the same amounts of reactants and crystallisation conditions, the only exception was that in this experiment no aluminium hydroxide was used. Upon opening of the autoclave it appeared that the extrudates were completely fallen apart into powder. The product was carefully recovered to avoid any losses during washing. After drying 18.10 grams were recovered, which is 9.5 wt % less than the amount of extrudates used (20.00 grams).

This experiment clearly shows that, in order to maintain and improve the strength of the extrudates, the presence of aluminium is essential.

EXAMPLE 3

In this Example the aluminium content of the aqueous potassium aluminate was varied and the mechanical strength of the products obtained was measured.

The procedure of Example 1 was followed and the compositions of the various potassium aluminate solutions (expressed as moles of oxides) ranged from $$2.85\ K_2O/(0-1.25)Al_2O_3/135\ H_2O.$$

The extrudates of zeolite L used as the starting material were binder-free zeolite L obtained according to the process of GB-A-8704365. They had a $SiO_2/Al_2O_3$ mole ratio of approx. 5.1. In all cases 30 grams of extrudate were treated with approximately 59 grams of aqueous potassium aluminate solution.

The results obtained for 6 runs with either no $Al_2O_3$ content or increasing $Al_2O_3$ content in the potassuim aluminate solution were as follows:

| | Synthesis | | | Product | | | | |
|---|---|---|---|---|---|---|---|---|
| Run | Mole $K_2O/$ $H_2O$ | $Al_2O_3$ content of liquor (moles/ 135 moles $H_2O$) | XRD-cryst. versus starting binder-free zeolite KL % | TGA % tot. ads. $p/p_o = 0.25$ | Measured $Si/Al_2$ ratio[2] | Crush Strength (ASTM D4179)[a] | lb/mm | (kg/mm) |
| 1 | 0.022 | nil (ie KOH treat) | | 6.1 | — | | —[b] | — |
| 2 | 0.022 | 0.25 | 97 | 10.2 | 3.9 | | 0.9 | (0.4) |
| 3 | 0.022 | 0.50 | 91 | 9.5 | 3.6 | | 2.0 | (0.9) |
| 4 | 0.022 | 0.75 | 91 | 6.8 | 3.5 | | 3.1 | (1.4) |
| 5 | 0.022 | 1.00 | 83 | 6.6 | 3.5 | | 2.0 | (0.9) |
| 6 | 0.022 | 1.25 | 81 | 6.6 | — | | — | — |
| 7 | 0.011 | 0.25 | 96 | 9.0 | — | | 1.5 | (0.7) |

[a]crush strength conventionally bound extrudates: 1.0 lb/mm (0.4 kg/mm)
crush strength starting binderfree zeolite L: 1.6 lb/mm
[b]particles disintegrated to powder The crush strength was measured as follows:
One particle was laid between two dies. The force on the die was increased slowly. The pressure needed for the crushing of the particle was read on a manometer and is called the "crush strength".

In order to reduce the influence of the length of the extrudates 10 particles of ca. 3 mm and 10 particles of ca. 5 mm length were measured.

It can be seen that significant increases in strength are achieved when there is at least 0.5 moles of $Al_2O_3$ per 135 moles of water (0.0037 moles/mole of water) in the aluminate treating solution.

EXAMPLE 4

The procedure of Example 1 was followed but in two runs with varying amounts of KOH and CsOH. When no potassium is present pollucite is formed instead of zeolite L, and as shown when both potassium and caesium are present zeolite L is formed by with some loss of crystallinity but with no significant contamination. The loss of crystallinity is believed to be due to the presence of caesium.

| | | | | | Product | | |
|---|---|---|---|---|---|---|---|
| | | | | | XRD | | |
| | synthesis Composition synthesis liquor (moles expressed as oxides) | | | | % cryst. versus starting | | TGA |
| Run | $K_2O$ | $Cs_2O$ | $Al_2O_3$ | $H_2O$ | extrudate | contaminants | % toluene adsorption |
| 1 | 1.44 | 1.43 | 0.75 | 134 | 68 | nil | 6.7 |
| 2 | 1.90 | 0.84 | 0.75 | 132 | 66 | nil | 5.4 |

I claim:

1. A process for preparing particles of Zeolite L of improved mechanical strength comprising:
   (a) providing binderless preformed particles of Zeolite L, said particles prepared by reacting silica-bound particles containing preformed Zeolite L crystallites present in said silica-bound particles at a level of up to 95 wt % with an alkaline solution containing a source of alumina to convert the silica binder to Zeolite L; and
   (b) reacting said binderless preformed particles with an aqueous alkaline solution containing a source of alkali metal, at least 50 mole % of which alkali metal is potassium, and aluminum present in said solution at a molar ratio of aluminum, expressed as $Al_2O_3$, to water of at least 0.0015.

2. The process of claim 1 wherein said Zeolite L crystallites present in said silica-bound particles of step (a) are in the form of cylinders with a mean diameter of at least 0.05 micron.

3. The process of claim 1 wherein said binderless preformed Zeolite L particles are in the form of tablets or extrudates.

4. The process of claim 1 wherein the alkali metal present in said aqueous alkaline solution of step (b) consists of potassium.

5. The process of claim 1 wherein the Zeolite L of step (a) is an aluminosilicate having the following formula, expressed as molar ratios of the constituent oxides in anhydrous form: $(0.9–1.3)M_{2/n}:Al_2O_3:XSiO_2$, wherein M is a cation of valence n and X=4 to 7.5.

6. The process of claim 1 wherein said aqueous alkaline solution of step (b) has an alkalinity, expressed as $K_2O/H_2O$ molar ratio, of from 0.007 to 0.028.

7. The process of claim 1 wherein said alkalinity is from 0.011 to 0.022.

8. The process of claim 1, wherein said alkali metal present in said aqueous alkaline solution of step (b) comprises potassium and at least one other alkali metal, the molar ratio of potassium to said at least one other alkali metal, expressed as oxide $K_2O/(M_2O+K_2O)$, being between 0.7 and 1.0, wherein M is said at least one other alkali metal.

9. The process of claim 1, wherein the molar ratio of aluminum, expressed as $Al_2O_3$, to water present in said aqueous alkaline solution of step (b) is at least 0.002.

10. The process of claim 9 wherein said molar ratio is between 0.002 and 0.006.

11. The process of claim 1 wherein said binderless preformed particles consist of a plurality of individual zeolite L crystallites held together without the use of a non-zeolite binder.

12. The process of claim 1 wherein said reaction in step (b) is conducted at a temperature of from 100° C. to 200° C. for at least 12 hours.

13. The process of claim 12 wherein said reaction is conducted for 15 to 96 hours.

14. Particles of Zeolite L having improved mechanical strength prepared by the process of claim 1.

15. A catalyst comprising a catalytically active metal and the Zeolite L particles of claim 14.

16. The catalyst of claim 15 wherein sid catalytically active metal is selected from the group consisting of platinum and palladium, and comprises an amount of 0.1 to 6.0 wt. % of said catalyst, based on the total weight of said catalyst.

17. The catalyst of claim 16 wherein said catalytically active metal comprises an amount of 0.1 to 1.5 wt. % of said catalyst, based on the total weight of said catalyst.

18. The catalyst of claim 17 wherein said zeolite L is in the potassium form and said catalytically active metal is platinum comprising an amount of 0.4 to 1.2 wt. % of said catalyst, based on the total weight of said catalyst.

* * * * *